United States Patent [19]

Heine et al.

[11] Patent Number: 5,859,687
[45] Date of Patent: Jan. 12, 1999

[54] BAR SKIASCOPE BEAM FIXABLE IN PARALLEL

[75] Inventors: Helmut Heine, Herrsching; Anton Schneider, Geisenbrunn; Otto H. Schmidt, Herrsching, all of Germany

[73] Assignee: Heine Optotechnik GmbH & Co. KG, Herrsching, Germany

[21] Appl. No.: 871,135

[22] Filed: Jun. 6, 1997

Related U.S. Application Data

[63] Continuation of Ser. No. 790,478, Jan. 29, 1997, abandoned.

[30] Foreign Application Priority Data

Jun. 28, 1996 [DE] Germany .................. 296 11 337.9

[51] Int. Cl.[6] .................................................. A61B 3/10
[52] U.S. Cl. ................................. 351/218; 351/216
[58] Field of Search .................... 351/218, 217, 351/216, 205, 246, 200

[56] References Cited

U.S. PATENT DOCUMENTS

| | | | |
|---|---|---|---|
| 2,501,438 | 3/1950 | Copeland | 88/20 |
| 3,602,581 | 8/1971 | Heine | 351/15 |
| 5,650,839 | 7/1997 | Sims | 351/218 |

OTHER PUBLICATIONS

Rassow, Bernhard; Ophthalmologisch–optische Instrumente, Ferdinand Enke Verlag Stuttgart, 1987, S. 36–41.

*Primary Examiner*—Hung X. Dang
*Attorney, Agent, or Firm*—Griffin, Butler, Whisenhunt & Szipl, LLP

[57] ABSTRACT

A bar skiascope that has lens slide for displacing a condenser lens along a direction of a light beam also includes a stop slide that can be displaced up to a predetermined maximum position in a displacement path of the lens slide, wherein the condenser lens is located precisely in a position for producing a substantially parallel beam, when the stop slide is in the maximum position, and a stop slide stop element, belonging to the stop slide, and a lens slide stop element, belonging to the lens slide, come into contact with each other.

14 Claims, 5 Drawing Sheets

BAR SKIASCOPE BEAM FIXABLE IN PARALLEL

This is a continuation application of application Ser. No. 08/790,478, filed Jan. 29, 1997, now abandoned.

BACKGROUND OF THE INVENTION

This invention relates to a bar skiascope of a type having a lens slide for displacing a condenser lens in front of a lamp inside a skiascope housing.

A skiascope, also called a retinoscope in international parlance, is a device used to assess objectively defective vision of an eye, and to determine eyeglass lenses needed to correct the defective vision. A type of skiascopy, also called retinoscopy in international parlance, has been known for decades, and is used worldwide in the field of ophthalmology because it can be used without regard to location, and because of its accuracy.

In the field of skiascopy, a distinction is made between bar skiascopy (bar retinoscopy) and point skiascopy (point retinoscopy), with bar skiascopy being used more often than point skiascopy.

A bar skiascope comprises mainly an incandescent lamp, a condenser lens, and a semireflecting mirror. Light generated by the incandescent lamp is made divergent, parallel, or convergent by displacement of the condenser lens, and is deflected via the mirror as a light band onto an eye to be examined. An examiner looks through the semireflecting mirror coaxially along the axis of a light beam, and observes light reflected from a fundus oculi of an eye. As he does so, he executes oscillating motions with the bar skiascope, so that the eye is alternately illuminated and not illuminated. The direction of movement and speed of movement of the observed reflex provide information about the type of vision defect. By placing corrective lenses in front of the eye, the reflexes change, until ultimately a condition characterized as alignment is achieved, in which the eye is fully corrected.

Over time, various techniques have been developed for using bar skiascopes, which are characterized by various examination parameters. For example, an examination distance may be a set, unchanging value, or it may be changed intentionally during the examination. In addition, an illumination beam can be divergent at the start of an examination and become convergent as the examination progresses, etc. A direction of the light band can also be set at any value by rotating the incandescent lamp through almost 360°.

In a common application, a beam path is made parallel for a brief time during an examination, in order to determine an axial position of astigmatism, for example, or to check axial correction already achieved using supplementary lenses. To that end, an examiner projects a light beam of a bar skiascope onto a wall at as great a distance as possible, and focuses the light band into a bar image. This procedure is time-consuming, since the examination must be interrupted, and it is imprecise, because parallel adjustment is usually impossible at a distance of only a few meters, usually. However, an adjustment that is not quite exactly parallel has an immediate impact on results of the examination because of a requirement for accuracy that is necessary in this examination method. This may result in an inaccurate or even erroneous diagnosis.

In a known skiascope, a locking device is provided as a device to fix the beam in a parallel position. In this design, a lens slide for displacing the condenser lens engages in a locked position for achieving a parallel beam position. This does make setting the parallel beam position considerably easier, but this locking in position impedes sliding transition from convergent to divergent ranges, and vice versa as is, needed for other examination techniques. Furthermore, convergence and divergence cannot be adjusted in an immediate vicinity of the locking position.

It is an object of this invention is to provide a bar skiascope which allows the fixing of a beam in a parallel-beam position that overcomes the stated disadvantages of fixing devices known in the prior art.

SUMMARY

According to the principles of this invention, a bar skiascope that has a lens slide for displacing a condenser lens along a direction of a light beam also includes a stop slide that can be displaced up to a predetermined maximum position in a displacement path of the lens slide, wherein the condenser lens is located precisely in a position for producing a substantially parallel beam, when the stop slide is in the maximum position, and a stop slide stop element, belonging to the stop slide, and a lens slide stop element, belonging to the lens slide, come into contact with each other.

BRIEF DESCRIPTION OF THE DRAWINGS

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views The drawings are not necessarily to scale, emphasis instead being placed upon illustrating principles of the invention in a clear manner.

DESCRIPTION OF THE PREFERRED EMBODIMENT

Figure 1:
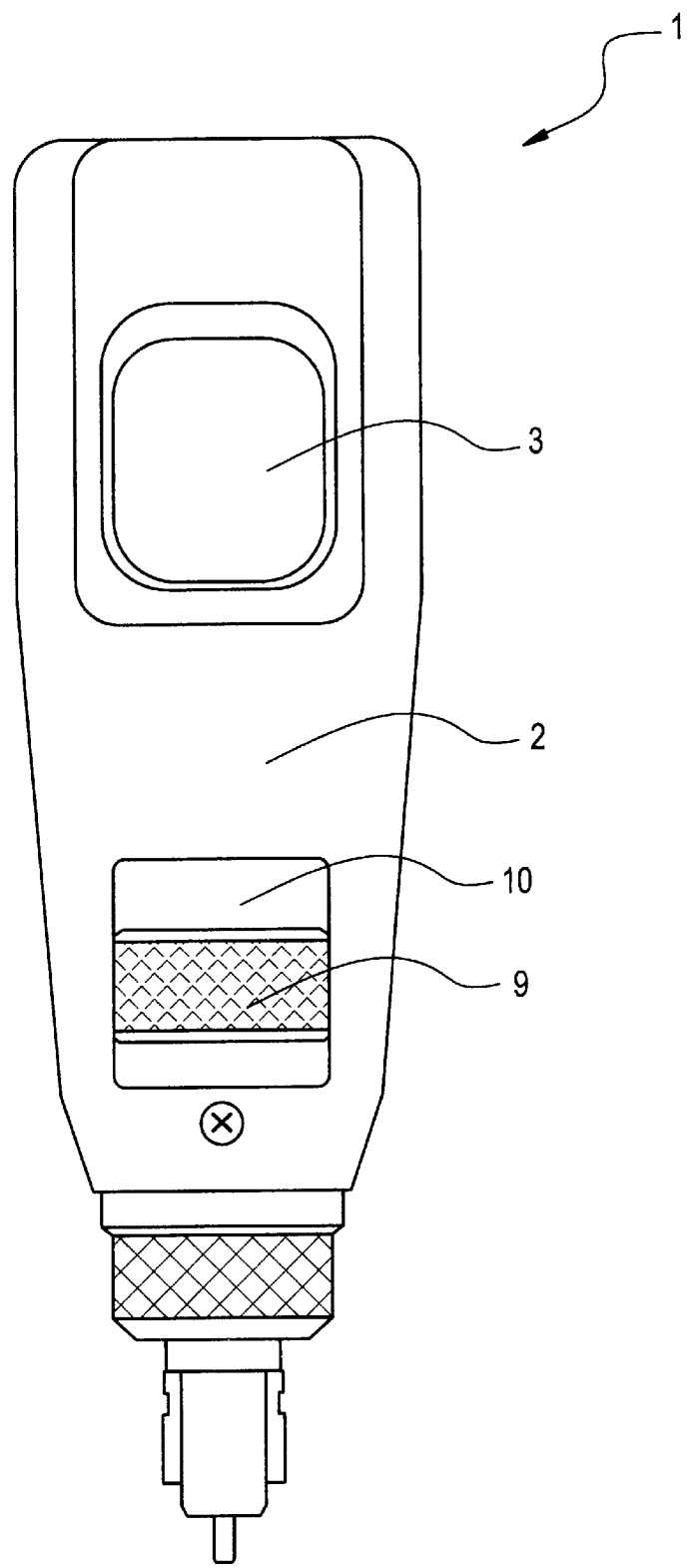
FIG. 1 front view, as seen by a patent, of a bar skiascope according to the invention.

FIG. 1 is a patient's view of a bar skiascope 1 in accordance with the invention. From the patient's perspective, the bar skiascope 1, in accordance with the invention, is indistinguishable from a conventional bar skiascope with an elongated skiascope housing 2 and a window 3 located in the skiascope housing 2, through which light is directed into A patient's eye.

Figure 2:
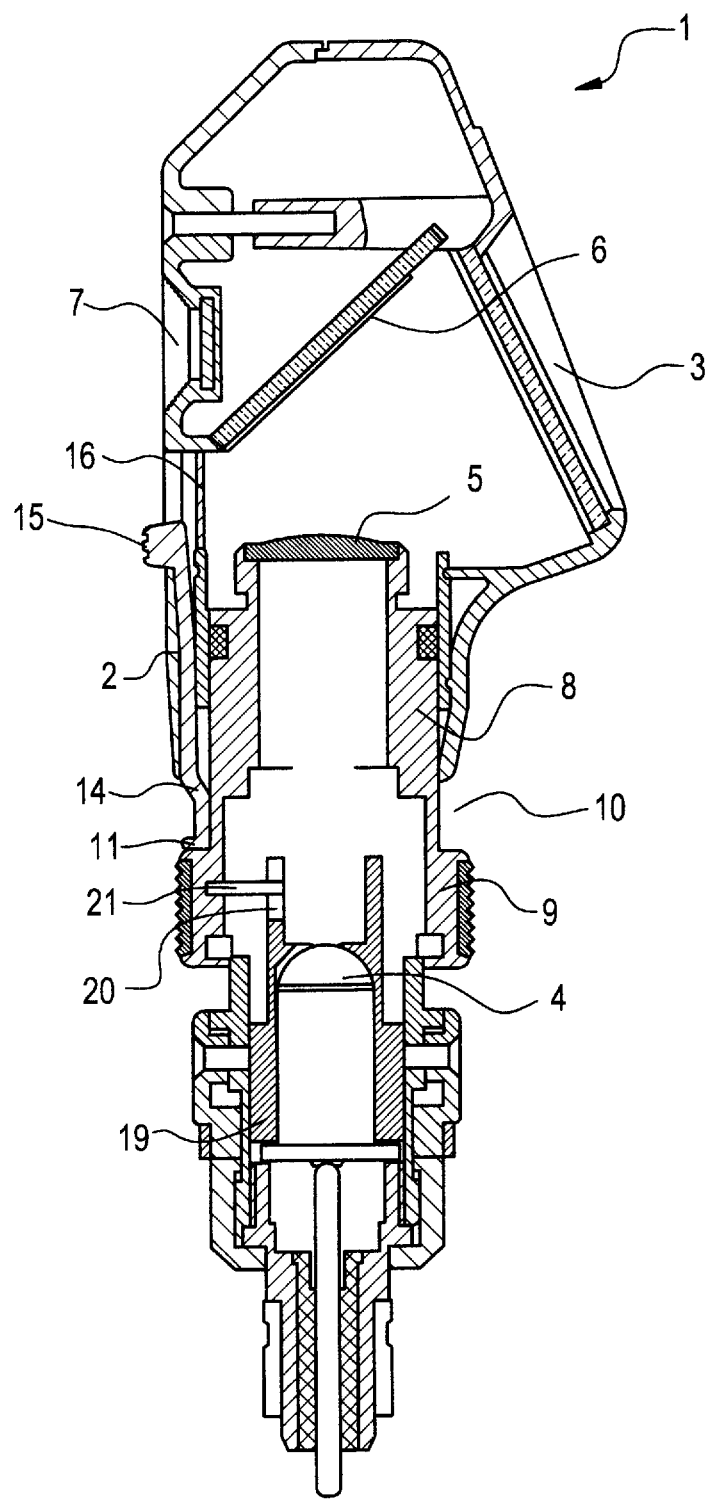
FIG. 2 is a side longitudinal cross sectional view of the bar skiascope of FIG. 1, according to this invention.
Figure 3:
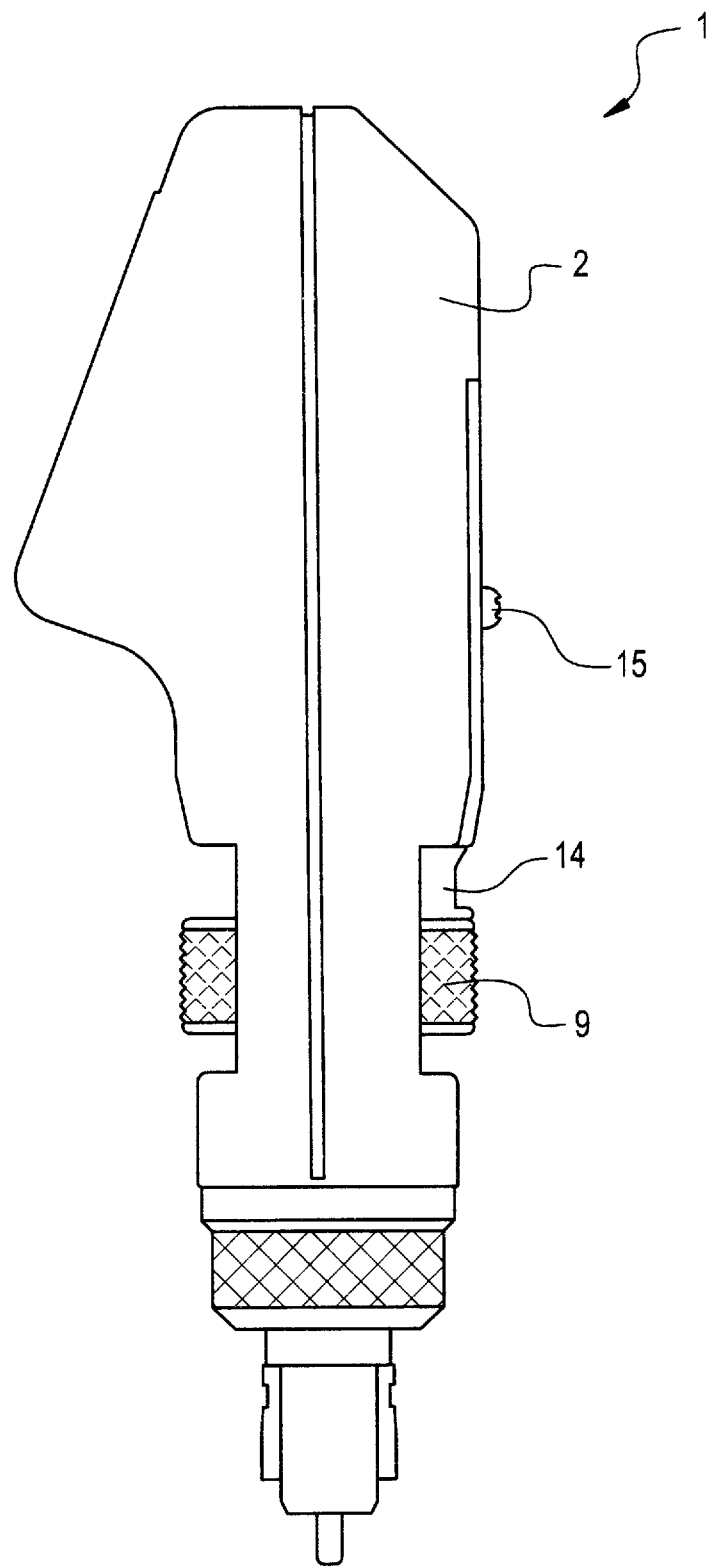
FIG. 3 is a side view of the other side of the bar skiascope of FIG. 1.

FIG. 2 is a side longitudinal section of the bar skiascope 1 in accordance with the invention. Inside the skiascope housing 2, there is an incandescent lamp 4. From the incandescent lamp 4, light passes through a condenser lens 5 and is reflected from a semireflecting (semi-light transmissive) mirror 6 (which are also located inside the skiascope housing 2), before passing through the window 3. A user can observe light reflected from a fundus of the patient's eye through an opening 7 in the skiascope housing 2, the semireflecting mirror 6, and the window 3.

The condenser lens 5 is rigidly attached to a lens slide 8. A lens-slide stop element 9 belonging to the lens slide 8 serves at the same time as a grip for manual displacement of the lens slide 8 along with the condenser lens 5, and for manually turning the incandescent lamp 4 about its longitudinal axis, as desired. The lens slide stop element 9 can be displaced up and down in a direction of displacement along a displacement path 10 inside an opening in the skiascope housing 2. A maximum length of the displacement path 10 is defined by a distance between stops 11 and 12 (see FIG. 4) and by a width of the lens slide stop element 9. In this manner, both a direction of displacement and a maximum length of a displacement distance of the condenser lens 5 is determined. The lens slide 8, along with the condenser lens 5, is fixed in place by force of static friction at any possible position of displacement, regardless of a spatial positioning or orientation of the skiascope 1, so that it cannot be displaced from whatever displacement position it is in without application of an additional force.

By displacing the condenser lens 5, light emitted by the incandescent lamp 4 is made divergent, parallel, or convergent, depending on a position of displacement of the condenser lens 5. The position for a parallel beam is approximately at a middle point along the maximum possible distance of displacement.

The incandescent lamp 4 is held by static friction in a rotatable cylindrical socket 19. In a wall of the socket, there is a groove 20 running parallel to an axis of the socket, into which fits a driving pin 21 that is attached to the lens slide stop element 9. When the lens slide stop element 9 is rotated, the pin 21, moves the socket 19 with it.

A length of the groove 20 is great enough so that the pin 21 remains engaged in any possible position of displacement of the lens slide 8.

A characteristic fixing device for fixing the lens slide 8 and the condenser lens 5 in the parallel beam position is described below for an embodiment of the bar skiascope 1 in accordance with the invention, with reference to FIGS. 2 through 5.

The fixing device comprises an essentially rectangular guide opening 13 in the skiascope housing 2 and a stop slide. From a user's perspective, the guide opening 13 is located at the center, above the opening for the lens slide stop element 9. A lengthwise direction of the guide opening 13 is identical to a lengthwise direction of the skiascope housing.

The stop slide has an elongated die bolt 14 and a guide lug 15 rigidly attached to the die bolt 14. The die bolt 14 is placed on the inside of the skiascope housing 2, and in this manner it is largely protected from any potential external mechanical forces that may result in its deformation. The guide lug 15, which is essentially cuboid in shape, fits into the guide opening 13 in such a way that along its length it essentially fills the width of the guide opening 13, and juts out from the skiascope housing 2.

A direction of displacement of the lens slide 8 and the stop slide is identical.

A support element 16 presses the die bolt 14 against the skiascope housing 2, laterally with respect to the direction of displacement. By displacing the guide lug 15 with his finger, the user can move the stop slide back and forth along the path predetermined by dimensions of the guide opening 13 and the guide lug 15. However, contact surfaces of the skiascope housing 2, the die bolt 14, and the support element 16 are designed so that the stop slide is affixed by static friction in any possible position, so that it cannot be displaced therefrom without application of additional force, regardless of a spatial orientation or positioning of the bar skiascope 1. Similarly, the lens slide 8 is held in position by static friction on the support element 16 and the skiascope housing 2, regardless of a spatial positioning or orientation of the bar skiascope 1. However, the static friction holding the lens slide 8 is smaller than the static friction affixing the stop slide. In this way, the stop slide is sure not to immediately move, without something further, when the user brings the lens slide stop element 9 into contact with the stop slide stop element 11.

Figure 4:
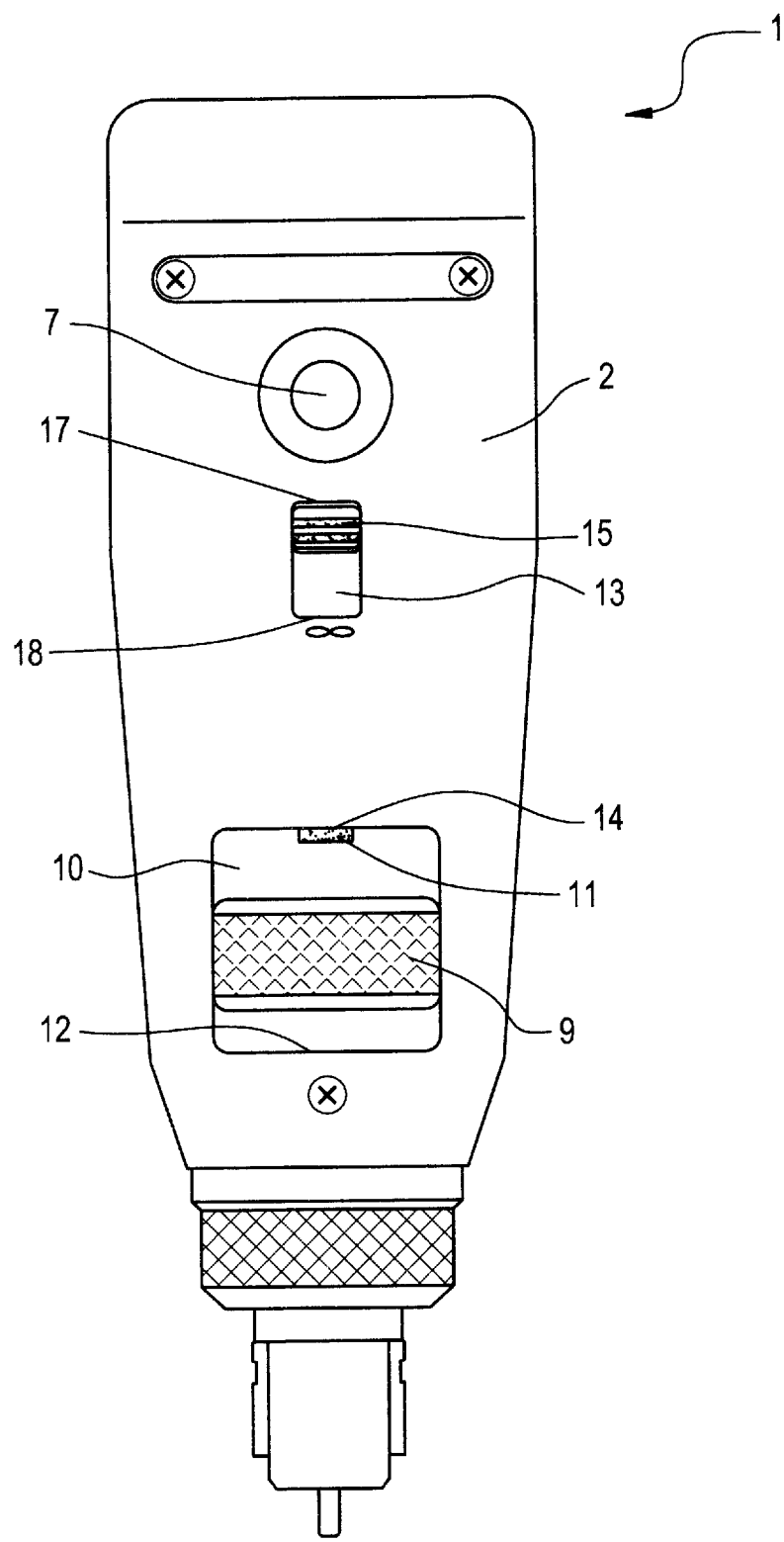
FIG. 4 is a back view, as seen by a doctor, of the bar skiascope of FIG. 1, with a stop slide in a first position.

FIG. 4 shows the stop slide in a first position, with the guide lug 15 at a first end 17 of the guide opening 13, opposite the lens slide element 9. In this first position, an end piece 11 of the die bolt 14, shaped as an angular element opposite the guide lug 15, forms the specified stop 11. Thus, this end piece is, at the same time, the stop slide stop element 11. The condenser lens 5 can be displaced back and forth along the specified maximum distance.

Figure 5:
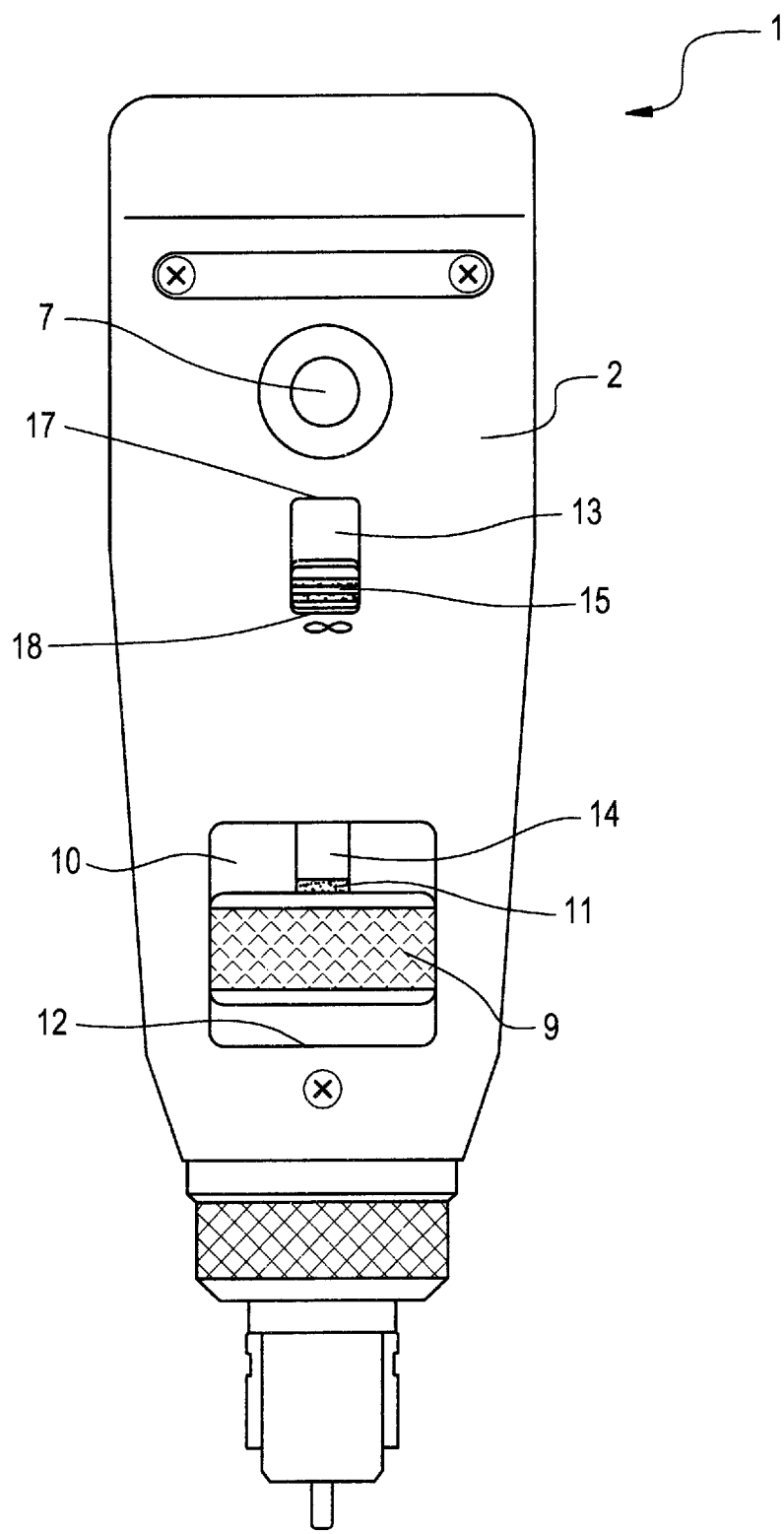
FIG. 5 is a view similar to FIG. 4, but with the stop slide in a second position and a lens slide in a position for producing a parallel beam.

FIG. 5 shows the stop element in a second position, with the guide lug 15 at a second end 18 of the guide opening 13, toward the lens slide stop element 9. In this second position, the die bolt 14 juts out into the displacement path 10 of the lens slide 8 and the lens slide stop element 9. The lens slide 8 and the condenser lens 5 can now be moved back and forth only along a distance whose length is smaller than the maximum specified length. The sizes of the lens slide element 9, the guide opening 13, and the stop slide are such that a position of displacement of the lens slide 8 at which the lens slide stop element 9 impacts against the stop slide stop element 11, is precisely at a position of the condenser lens 5 that produces a parallel beam position.

In the illustrated embodiment of the bar skiascope 1, according to the invention, the lens slide 8 is displaced from the divergent range A toward and against the stop slide. Since the stop slide is sufficiently fixed in position by static friction described above, regardless of its positioning, an advantage is thus achieved that stop positions, and thereby condenser lens positions, can be fixed as desired in the convergent range.

A bar skiascope according to this invention provides easy adjustment to the parallel beam position. At the same time, it simplifies a sliding transition between the convergent and divergent ranges. Adjustment of convergence and divergence, even in an immediate vicinity of the setting for the parallel beam position, is possible.

The embodiment recited as in claim 2 has the special advantage that a person using the lens slide, even after adjusting to the parallel beam position, can move, with even smoothness, into both the divergent and convergent ranges, without having to actuate a stop slide separately.

The invention claimed is:

1. A bar skiascope having
   a skiascope housing,
   an incandescent lamp placed inside the skiascope housing,
   a condenser lens placed in front of the incandescent lamp inside the skiascope housing in a direction of radiation of a light beam from the incandescent lamp, and
   a lens slide connected to the condenser lens, for displacing the condenser lens along a displacement path of the lens slide relative to the skiascope housing in the direction of radiation of the light beam,
   a stop slide supported by the skiascope housing for being displaced in a stop-slide displacement path relative to said housing by application of force with a finger to a predetermined first stop-slide maximum position in the displacement path of the lens slide and for being affixed relative to said housing upon removal of said force so as to determine a first lens-slide maximum position at one end of said displacement path of said lens slide.

2. A bar skiascope as in claim 1, wherein the lens slide and the stop slide have a common direction of displacement.

3. A bar skiascope as in claim 2, wherein:
the stop slide comprises an elongated die bolt and a guide lug connected to the die bolt;
the skiascope housing defines a guide opening, with the guide lug fitting into the guide opening;
the guide lug can be moved back and forth between a first position at a first end of the guide opening and a second position at a second end of the guide opening;
a stop-slide stop element is at an end of the die bolt directed toward lens-slide stop element; and
the guide lug is placed at an end of the die bolt opposite the end at which the stop-slide stop element is located.

4. A bar skiascope as in claim 2, wherein the stop slide is pressed laterally with respect to the direction of displacement, against an inner wall of the skiascope housing by a support element located inside the skiascope housing.

5. A bar skiascope as in claim 1, wherein, when the stop slide is in the first stop-slide maximum position, the condenser lens is displaceable by means of the lens slide within a range for producing divergent beam path without contacting the stop slide.

6. A bar skiascope as in claim 1, wherein a stop-slide stop element of the stop slide is designed as an angled element.

7. A bar skiascope as in claim 1, wherein the stop slide is located substantially inside the skiascope housing.

8. A bar skiascope as in claim 1, wherein the stop slide is for being affixed, in its first stop-slide maximum position and in a second stop-slide maximum position furthest removed from the displacement path of the lens slide, so that, regardless of orientation of the bar skiascope, the stop slide cannot be displaced from these positions without said application of force.

9. A bar skiascope as in claim 8, wherein the stop slide is affixed in position by static friction acting on the stop slide.

10. A bar skiascope as in claim 9, wherein the static friction acting on the stop slide when it is affixed is greater, at least in the first stop-slide maximum position, than is static friction acting on the lens slide in any position of the lens slide.

11. A bar skiascope as in claim 1, wherein movement of the lens slide along the displacement path of the lens slide in a first direction causes the lens to produce light from the skiascope housing which changes from being divergent to being parallel to being convergent.

12. A bar skiascope as in claim 1, wherein the first stop-slide maximum position determines a first lens-slide maximum position whereat the lens produces parallel light.

13. A bar skiascope as in claim 1, wherein the lens slide is rotatable for rotating the incandescent lamp through a displacement angle about an axis parallel to the direction of radiation from the incandescent lamp.

14. A bar skiascope having
a skiascope housing,
an incandescent lamp placed inside the skiascope housing,
a condenser lens placed in front of the incandescent lamp inside the skiascope housing in a direction of radiation of a light beam from the incandescent lamp, and
a lens slide connected to the condenser lens, for displacing the condenser lens along a displacement path of the lens slide in the direction of radiation of the light beam,
a stop slide supported by the skiascope housing for displacement to a predetermined position in the displacement path of the lens slide; wherein:
the lens slide and the stop slide have a common direction of displacement;
the stop slide comprises an elongated die bolt and a guide lug connected to the die bolt;
the skiascope housing defines a guide opening, with the guide lug fitting in the guide opening;
the guide lug can be moved back and forth between a first position at a first end of the guide opening and a second position at a second end of the guide opening;
a stop slide stop element is at an end of the die bolt directed toward a lens slide stop element; and
the guide lug is placed at an end of the die bolt opposite the end at which the stop slide stop element is located.

* * * * *